US009522202B1

United States Patent
Ahiska et al.

(10) Patent No.: US 9,522,202 B1
(45) Date of Patent: Dec. 20, 2016

(54) VARIABLE PLASMA GENERATOR FOR USE WITH LOW TEMPERATURE STERILIZERS

(71) Applicant: GOA TEKNOLOJI DANISMANLIK ELEKTRONIK, IMALAT TICARET ITHALAT IHRACAT A. S., Ankara (TR)

(72) Inventors: Fatih Ahiska, Ankara (TR); Yavuz Ahiska, Surrey (GB); Tolga Ahiska, Ankara (TR)

(73) Assignee: GETINGE STERICOOL MEDIKAL ALETLER SAN, VE TIC. A.S., Sincan, Ankara (TR)

( * ) Notice: Subject to any disclaimer, the term of this patent is extended or adjusted under 35 U.S.C. 154(b) by 45 days.

(21) Appl. No.: 14/269,526

(22) Filed: May 5, 2014

Related U.S. Application Data

(60) Provisional application No. 61/820,384, filed on May 7, 2013.

(51) Int. Cl.
*A61L 2/14* (2006.01)

(52) U.S. Cl.
CPC .............................. *A61L 2/14* (2013.01)

(58) Field of Classification Search
CPC ........................................................ A61L 2/14
See application file for complete search history.

(56) References Cited

U.S. PATENT DOCUMENTS

| | | | |
|---|---|---|---|
| 3,383,163 A | 5/1968 | Menashi | |
| 3,701,628 A * | 10/1972 | Ashman et al. | A61L 2/14 422/23 |
| 4,169,123 A | 9/1979 | Moore et al. | |
| 4,169,124 A | 9/1979 | Forstrom et al. | |
| 4,642,165 A | 2/1987 | Bier | |
| 4,643,876 A | 2/1987 | Jacobs et al. | |
| 4,744,951 A | 5/1988 | Cummings et al. | |
| 4,756,882 A | 7/1988 | Jacobs et al. | |
| 4,956,145 A | 9/1990 | Cummings et al. | |
| 5,203,945 A * | 4/1993 | Hasegawa | H01J 37/32935 118/723 R |

(Continued)

FOREIGN PATENT DOCUMENTS

WO   WO2005067984   7/2005

OTHER PUBLICATIONS

Beatriz Unger-¬ Bimczok, Volker Kottke, Christian Hertel, Johannes Rauschnabel, "The Influence of Humidity, Hydrogen Peroxide Concentration, and Condensation on the Inactivation of Geobacillus Stearothermophilus Spores with Hydrogen Peroxide Vapor", Journal of Pharmaceutical Innovation, vol. 3, No. 2 (Jun. 28, 2008), pp. 123-133.

(Continued)

*Primary Examiner* — Regina M Yoo
(74) *Attorney, Agent, or Firm* — Thomas | Horstemeyer, LLP

(57) ABSTRACT

In a low temperature hydrogen peroxide gas plasma sterilizer, plasma within the sterilization chamber contributes to the sterilization process and decomposes the sterilant used at the end of a sterilization programs. The plasma however the must be properly profiled otherwise undesired surface etching may occur on the sensitive medical apparatus. This application describes a novel plasma control method and apparatus which minimize the harmful side effects plasma on the medical apparatus during a sterilization program.

2 Claims, 13 Drawing Sheets

(56) References Cited

U.S. PATENT DOCUMENTS

| | | | | |
|---|---|---|---|---|
| 5,303,139 | A | * | 4/1994 | Mark .............. H01J 37/32018 204/298.08 |
| 5,474,648 | A | * | 12/1995 | Patrick ............ H01J 37/32082 156/345.28 |
| 5,512,244 | A | * | 4/1996 | Griffiths ................ A61L 2/14 422/22 |
| 5,556,549 | A | * | 9/1996 | Patrick ............ H01J 37/32082 118/712 |
| 6,060,019 | A | * | 5/2000 | Spencer ................ A61L 2/14 34/257 |
| 6,104,487 | A | * | 8/2000 | Buck .................... G01N 21/68 216/60 |
| 6,269,680 | B1 | * | 8/2001 | Prieve .................. A61L 2/208 250/373 |
| 6,383,554 | B1 | * | 5/2002 | Chang .............. H01J 37/3299 427/10 |
| 6,746,647 | B2 | * | 6/2004 | Kohler .................. A61L 2/14 422/1 |
| 6,841,124 | B2 | * | 1/2005 | Chien .................... A61L 2/14 422/105 |
| 8,158,525 | B2 | | 4/2012 | Takahashi |
| 8,647,585 | B2 | * | 2/2014 | Hancock ................ A61L 2/14 422/186 |
| 8,663,555 | B2 | * | 3/2014 | Shiosawa ................ A61L 2/02 422/22 |
| 2004/0226658 | A1 | * | 11/2004 | Lai .................. H01J 37/32431 156/345.48 |
| 2004/0262146 | A1 | * | 12/2004 | Platt, Jr. ................ A61L 2/14 204/164 |
| 2006/0162741 | A1 | * | 7/2006 | Kurunczi ................ A61L 2/14 134/1.1 |
| 2010/0296977 | A1 | * | 11/2010 | Hancock ................ A61L 2/14 422/186 |
| 2014/0066838 | A1 | * | 3/2014 | Hancock ................ A61L 2/14 604/23 |
| 2015/0056107 | A1 | * | 2/2015 | Hancock ................ A61L 2/14 422/186 |

OTHER PUBLICATIONS

James R. Rickloff "Factors Influencing Hydrogen Peroxide Gas Sterilant Efficacy", Advanced Barrier Inc. Nov. 12, 2008.

Sterrad NX Sterilization System—User's Guide (REF 99920), Advanced Sterilization Products—a Johnson & Johnson Company, Division of Ethicon, Inc., Sep. 2008.

Sterrad 100NX Sterilizer System—User's Guide (REF 99970), Advanced Sterilization Products—a Johnson & Johnson Company, Division of Ethicon, Inc., Feb. 2008.

Sterrad 100 Sterilization System Service Guide, Advanced Sterilization Products Services, Inc., 1997.

Jacobs, Paul T., Sterrad 100S Sterilization System, Advanced Sterilization Products—a Johnson & Johnson Company, Division of Ethicon, Inc., 1999.

Sterrad 100NX Sterilization System—Service Troubleshooting Guide, Advanced Sterilization Products—a Johnson & Johnson Company, Division of Ethicon, Inc., Jun. 2007.

* cited by examiner

Figure 8 *(Figure 107 modified to accommodate a accurate pump)*

VARIABLE PLASMA GENERATOR FOR USE WITH LOW TEMPERATURE STERILIZERS

CROSS-REFERENCE TO RELATED APPLICATION

This application claims priority to U.S. provisional application entitled, "Novel Variable Plasma Generator for Use with Low Temperature Sterilizers," having appl. No. 61/820,384, filed May 7, 2013, which is entirely incorporated herein by reference.

BACKGROUND

The present application relates generally to sterilization of medical apparatus using both hydrogen peroxide vapor as sterilant and a glow discharge. The glow discharge (plasma) when activated within the sterilization chamber contributes to the sterilization and decomposes the sterilant at the end of a sterilization program. The glow discharge however the must be properly controlled otherwise undesired surface etching may occur on the sensitive medical apparatus. This application describes a novel plasma control method and apparatus which minimize the harmful side effects plasma on the medical apparatus during a sterilization program.

Note that the points discussed below may reflect the hindsight gained from the disclosed inventions, and are not necessarily admitted to be prior art.

Some background information can be found in the following documents, all of which are hereby incorporated by reference: Beatriz Unger-Bimczok, Volker Kottke, Christian Hertel, Johannes Rauschnabel, "The Influence of Humidity, Hydrogen Peroxide Concentration, and Condensation on the Inactivation of *Geobacillus stearothermophilus* Spores with Hydrogen Peroxide Vapor", Journal of Pharmaceutical Innovation, Vol. 3, No. 2 (28 Jun. 2008), pp. 123-133; James R. Rickloff "Factors Influencing Hydrogen Peroxide Gas Sterilant Efficacy", Advanced Barrier Inc. Nov. 12, 2008; U.S. Pat. Nos. 4,169,123, 4,169,124, 4,643,876, 4,756,882, 4,956,145, 4,642,165, and 4,744,951; PCT application WO 2005/067984; the Sterrad NX Sterilizer user and service manuals (from Advance Sterilization Products); and the Sterrad 100S Sterilizer user manual and service manuals.

Medical instruments were traditionally sterilized either with heat, such as is provided by steam, or a chemical, such as formaldehyde or ethylene oxide in the gas or vapor state. Each of these methods has drawbacks. Many medical devices, such as fiberoptic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long.

Sterilization using liquid hydrogen peroxide solution has been found to require high concentration of sterilant, extended exposure time and/or elevated temperatures. However, sterilization using hydrogen peroxide vapor has been shown to have some advantages over other chemical sterilization processes (see, e.g., the '123 and '124 documents cited above).

The combination of hydrogen peroxide with a plasma provides certain additional advantages, as disclosed in the '876 document cited above. The '882 document cited above discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized together with the reactive particles generated by plasma act together to sterilize the articles even more efficiently.

However, these methods of combining hydrogen peroxide vapor with a plasma, while useful in "open" systems, have been found to be inadequate to effect sterilization in articles having diffusion-restricted areas, since the methods are dependent upon diffusion of the sterilant vapor into close proximity with the article before sterilization can be achieved. Thus, in order to use these methods on articles with long, narrow lumens, it has been necessary to use high concentration of sterilant, extended exposure time, and/or elevated temperatures.

The sterilization of articles containing diffusion-restricted areas, such as long narrow lumens, presents a special challenge for hydrogen peroxide vapor that has been generated from an aqueous solution of hydrogen peroxide, because: (i) water ($H_2O$) has a higher vapor pressure than hydrogen peroxide ($H_2O_2$), and will vaporize faster than hydrogen peroxide from an aqueous solution; (ii) water has a lower molecular weight than hydrogen peroxide and will diffuse faster than hydrogen peroxide in the vapor state.

Consequently, when an aqueous solution of hydrogen peroxide is vaporized, the innermost locations in a diffusion-restricted lumen will initially see an enhanced $H_2O:H_2O_2$ ratio. This can lead to condensation of water vapor on the surface of the material to be sterilized before sufficient impingement of hydrogen peroxide has reached the innermost locations. The liquid-phase water then becomes a barrier to the penetration of hydrogen peroxide vapor into diffusion restricted areas, such as small crevices and long narrow lumens.

The '145 document cited above discusses the efficacy of highly concentrated hydrogen peroxide for the safe sterilization. The '067984 document discusses the problem of condensed water vapor blocking the diffusion of the sterilant to the bacteria lying on the surface of the material to be sterilized. The Unger document cited above explains the influence of humidity, hydrogen peroxide concentration, and the condensation of the water vapor in detail.

One cannot solve the problem by using more concentrated hydrogen peroxide, since concentrated solutions of hydrogen peroxide, i.e., greater than 60% by weight, can be hazardous, due to the oxidizing nature of the solution. Decomposition of liquid hydrogen peroxide is very exothermic, and releases large volumes of gas, so that stability is a serious concern. Highly concentrated liquid hydrogen peroxide is so energetic that it has been used as a monopropellant for rocket engines. Moreover, highly concentrated hydrogen peroxide can form unstable reaction products with minor contaminants (such as fingerprint grease), and those reaction products can be a further source of instability.

The above-cited documents '165 (Bier) and '951 (Cummings et al.) both attempt to address this problem. Bier attempts to solve the problem by metering small increments of a hydrogen peroxide solution onto a heated surface to ensure that each increment is vaporized before the next increment is added. This helps to eliminate the difference in the vapor pressure and volatility between hydrogen peroxide and water, but it does not address the fact that water diffuses faster than hydrogen peroxide in the vapor state.

Cummings describes a process for concentrating hydrogen peroxide from a relatively dilute solution of hydrogen peroxide and water and supplying the concentrated hydrogen peroxide in vapor form to a sterilization chamber. The process involves vaporizing a major portion of the water from the solution and removing the water vapor produced before injecting the concentrated hydrogen peroxide vapor into the sterilization chamber as shown in FIG. 1A.

FIG. 1A shows the apparatus proposed by Cummings, which includes a vaporizing chamber 7 having any well-known means 3 for injecting into chamber 7 a predetermined amount of a solution of hydrogen peroxide and water. Chamber 7 may be controllably heated by any well-known means. Chamber 7 has an outlet port 2 through which vapors may be exhausted from chamber 7 by means of a vacuum. Port 2 may be opened or closed by valve 1. Chamber 7 also has an outlet port 4 leading through passage 6 to a sterilization chamber 8. Passage 6 may be open or closed by valve 5.

The process is initiated by the injection into evacuated chamber 7 of predetermined amount of a liquid solution of hydrogen peroxide and water through injection means 3. When valve 5 is closed and valve 1 is open; vacuum is applied to chamber 7 to evacuate air. Chamber 7 is heated until the desired temperature within chamber 7 is reached; that temperature is such that, when taken with the pressure within chamber 7, a portion of water in the form of vapor will be forced to evaporate from a solution of liquid hydrogen peroxide solution present in chamber 7. Conditions are created within chamber 7 to cause the preferential vaporization of water from the solution and the vapor formed thereby is withdrawn from chamber 7 through port 2. At a point in time when a major portion of the water has been vaporized and withdrawn, but before a significant quantity of hydrogen peroxide has vaporized and been withdrawn, valve 1 is closed. What remains in chamber 7 is a hydrogen peroxide-water solution enriched in hydrogen peroxide, specifically greater than 40% hydrogen peroxide by weight, preferably 50 to 80% by weight. Vaporization of this enriched solution continues within chamber 7 and then valve 5 is opened to admit the vapors formed thereby to evacuated sterilization chamber 8. With a substantial amount of the water having been removed, the hydrogen peroxide vapor sterilant is able to disperse itself throughout the sterilizer and penetrate wraps and tubes without encountering a barrier effect that otherwise would have been present by reason of the effects of the present of water discussed above. Thus, the effective concentration of hydrogen peroxide vapor at the point of attack on the goods to be sterilized is markedly enhanced by the process.

Advance Sterilization Products, a division of Johnson and Johnson initially offered Sterrad 100S plasma sterilizer which use 59% wt hydrogen peroxide as sterilant.

Couple of years ago Advance Sterilization Products introduced the more advanced Sterrad 100NX Sterilizer which employs Cummings method of delivering hydrogen peroxide to sterilize devices within the sterilization chamber. In this apparatus a 59% wt aqueous solution of hydrogen peroxide is injected into the delivery system condenser where it is concentrated and then introduced into the chamber. This modified process concentrates the 59% hydrogen peroxide to above 80% nominal hydrogen peroxide (by selectively vaporizing and removing water) prior to being transferred into the sterilization chamber. Sterrad 100NX range have shorter sterilization cycles and higher lumen sterilization specifications.

Although Sterrad NX range provides sterilization efficacy recently some medical device manufacturers like Inutitive no longer recommends concentrated plasma sterilizers for their devices as they have reported that exposure to high concentration hydrogen peroxide vapor damages some of their endoscopes.

Further some sensitive endoscope manufacturers have required customized sterilization programs for their devices in order to minimize the sterilant vapor damage on their equipment.

The use of plasma to sterilize containers was suggested in U.S. Pat. No. 3,383,163. Plasma is an ionized body of gas which may be generated by the application of radio frequency power. The ionized gas will contact microorganisms on the surfaces of the items to be sterilized and effectively destroy the microorganisms. As mentioned above (006) the combination of hydrogen peroxide with a plasma provides certain additional advantages namely helping the sterilisation process by generating DNA destroying free radicals and UV light and at the end of the sterilization cycle by decomposing the harmful hydrogen peroxide sterilant.

Plasma generated at atmospheric pressure or at higher pressures are called "arcs" or high temperature plasma and may involve temperatures in excess of 1000.degree. C. Plasma generated at reduced pressures are called "glow discharge" or low temperature plasma and involve temperatures of a few tenths to a few hundred degrees centigrade (plasma glow because light is emitted as these excited neutral particles relax to a lower energy state). The low temperature plasma described in '876 is generated at pressures of less than 10 Torr and generally involves temperatures of less than 100 degree C.

The plasma power used in a sterilizer may be continuous or pulsed, that is, the power may be applied continuously to the plasma or the plasma may be pulsed by activating the power in a cyclic manner while maintaining the pressure of the plasma constant. The U.S. Pat. No. '876 describes a pulsed plasma to prevent the overheating of the gas within the chamber as well as preventing the overheating of objects that may be desired to be sterilized continuous plasma may be employed if there is little danger of overheating the item to be sterilized.

A plasma contains positive ions, electrons, neutral gas atoms or molecules, UV light and also excited gas atoms and molecules, which can carry a large amount of internal energy. All of these species can and do interact with any surface placed in contact with the plasma. By choosing the gas mixture, power, pressure etc. we can quite precisely tune, or specify, the effects of the plasma upon the surface. For this reason plasma is also widely used in the industry for etching purposes for silicon processing to PCB manufacturing (see http://en.wikipedia.org/wiki/Plasma_etching). For example the plasma etching method described U.S. Pat. No. 8,158,525 generally involves an etching step of placing, on a stage in a chamber, a substrate in which a prescribed mask pattern is formed by a protective film on a surface of a material to be etched, generating a plasma in the chamber while supplying processing gas to the chamber, and etching a portion of the material corresponding to an opening portion in the mask pattern. This etching occurs as a result of highly energised ions (usually heavy gas is preferred) bombarding a giving surface and damaging it. As stated above in the plasma process is employed in low temperature plasma sterilisers to sterilise sensitive medical apparatus by generating free-radicals and decomposing the harmful sterilant. However the resultant unavoidable etching as an unintended consequence needs to be minimized. Further many modern medical apparatus use materials based on polymers which under bombardment of energised ions could undergo physical changes and become more brittle etc losing its desirable properties for the task they were designed for.

The current invention disclose a novel method and an apparatus wherein: (i) the glow discharge plasma power is carefully profiled to execute the its task while minimize and etching damage. During the pre-conditioning plasma phase of a typical sterilisation cycle prior to exposing the medical apparatus to the sterilant the low pressure (54 FIG. 3) the vacuum within the sterilisation chamber contains pre-dominantly air molecules. During this phase plasma generates a controllable homogenous heat up to 55 degree C. and generates UV and free radicals which all contribute to the sterilisation. When the glow discharge is applied again at a later phase of the sterilisation program (64 in FIG. 3) the primary function of the plasma is to decompose the hydrogen peroxide and the secondary being to contribute to the sterilisation via the UV and free radicals generated. The current invention describes an methodology and an apparatus to maximise the above mentioned positive effects of the plasma during different phases of the sterilisation cycle while minimising its negative effect of causing a unintended etching on the medical apparatus to be sterilized. The said plasma power control is particularly challenging in the post sterilant diffusion phase as the RF generator output level applied must be sufficiently high to generate and sustain the plasma for generation of free radicals and more importantly the full decomposition of the sterilant hydrogen peroxide before opening of the door of the chamber but low enough to minimize and etching damage.

The U.S. Pat. No. '876 is silent on the etching however describes a method to control the power control output of the RF generator by turning the power of the generator in a pulsed sequence (the pulsing sequence is the ratio of power on to power off) which was varied over a range to prevent overheating any object. Said patent mentions a pulse sequence with a 1:2 pulsed plasma, power would be applied for 0.5 milliseconds and then turned off and applied again 1.0 milliseconds later.

The '876 patent however does not address the etching and polymer degeneration caused by the plasma in the sterilisation chamber. The pulsing in the method means turning the full power of the RF generator on and off. This continuous surge of power each time the plasma is retriggered would still generate bursts of high energy ions which continue stress the sensitive materials (polymers etc) used in medical apparatus and undesirable etching effect in all materials.

The current invention profiles the power of the RF generator in a manner to optimise its use in a low temperature sterilizer by
(i) employing a pulse width modulation to adjust the plasma power after the full power application to initiate an effective plasma state.
(ii) Monitoring the plasma within the chamber so that the glow discharge continuously present and re-initiate if it extinguished.
(iii) Applying different RF power characteristic when the gas content of the plasma is different phases of sterilisation process.

BRIEF DESCRIPTION OF THE DRAWINGS

The disclosed inventions will be described with reference to the accompanying drawings, which show important sample embodiments and which are incorporated in the specification hereof by reference, wherein.

DETAILED DESCRIPTION OF SAMPLE EMBODIMENTS

In a hydrogen peroxide vapor plasma sterilizer, the concentration of the hydrogen peroxide sterilant is an important factor in determining sterilization efficacy. The present application describes sterilizers, and sterilization methods, which use a multi level injector-concentrator and a novel plasma generator. This arrangement provides accurate control of concentration of the liquid-phase hydrogen peroxide, prior to vaporization of the liquid sterilant for release into the sterilization chamber of the sterilizator. This increases the reliability and efficacy of the sterilization cycle. The novel plasma generator protects disclosed reduces any harmful effect of high energy plasma on the sensitive medical apparatus to be sterilized.

This application describes new devices and methods which increase the reliability and efficacy of the sterilization cycle in an hydrogen peroxide gas plasma sterilization system by increasing and controlling the concentration of the liquid sterilant within the device, without requiring any handling or transportation of highly concentrated sterilant.

The numerous innovative teachings of the present application will be described with particular reference to presently preferred embodiments (by way of example, and not of limitation). The present application describes several inventions, and none of the statements below should be taken as limiting the claims generally.

The hydrogen peroxide gas plasma sterilization cycle is well understood and documented.

Figure 2:
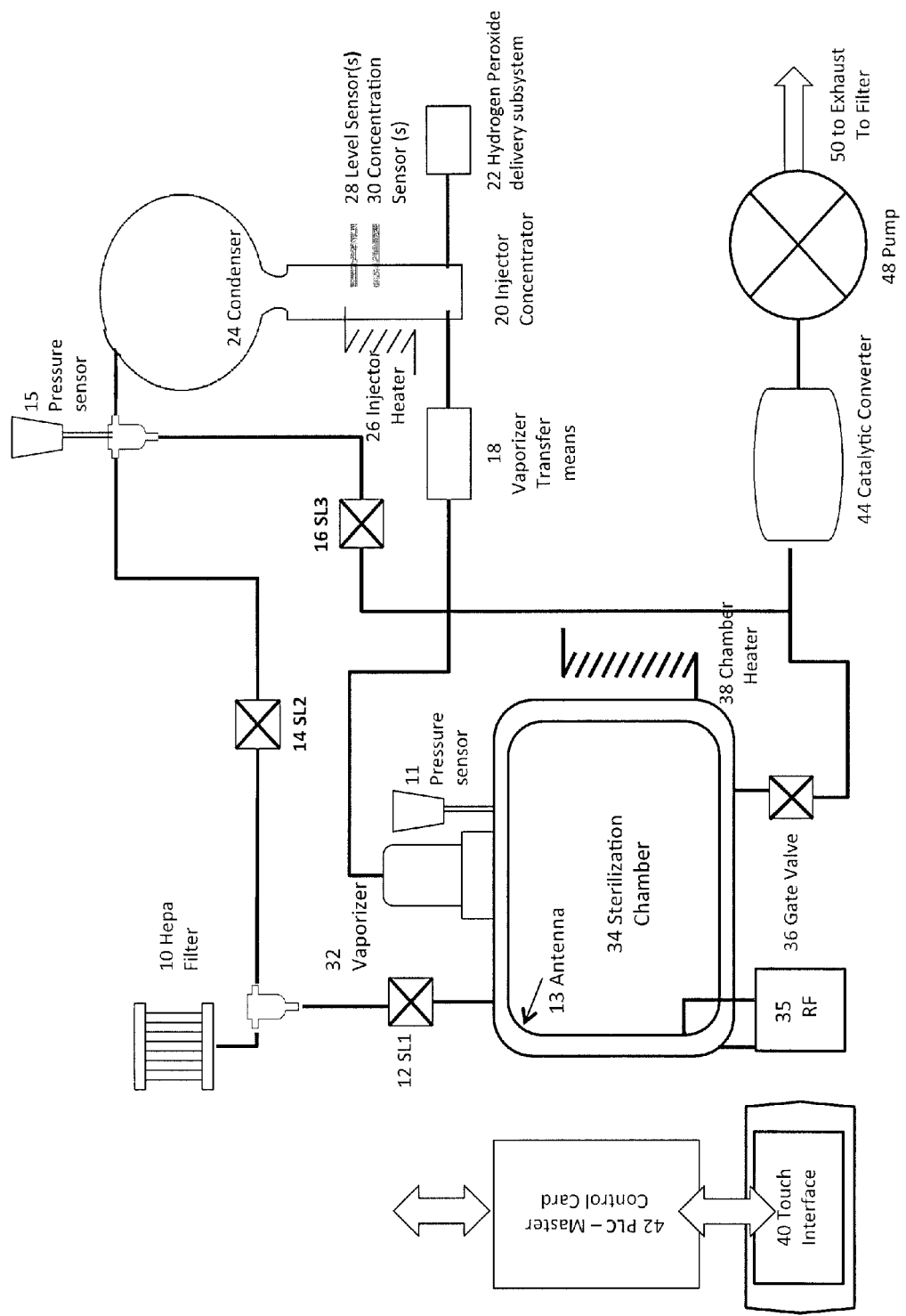
FIG. 2 shows the schematic of preferred embodiment of the hydrogen peroxide injector concentrator as deployed in a typical sterilizer configuration.
Figure 3:
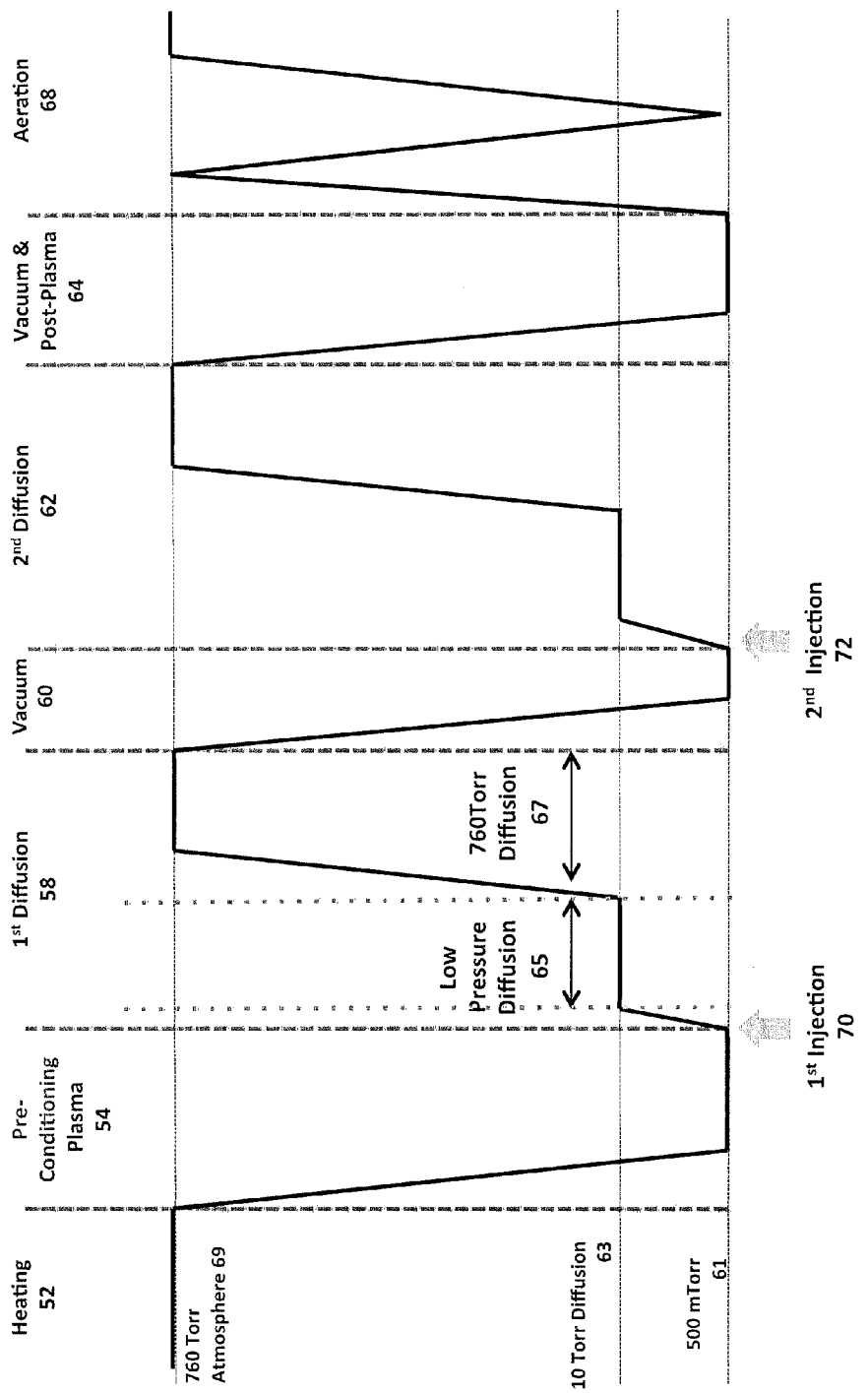
FIG. 3 shows pressure curve within the sterilization chamber during a typical full hydrogen peroxide gas plasma sterilization cycle.

FIG. 2 shows the schematic of preferred embodiment of the hydrogen peroxide injector-concentrator as deployed in a typical sterilizer, and FIG. 3 shows the state of the sterilization chamber during a typical sterilization cycle. In a typical cycle the washed and dried medical instruments to be sterilized are packed into sealed tyvek pouches and placed into the heated sterilization chamber 34 of the sterilizer. During the heating process 52 the temperature within the chamber is increased to around 48-55 degree centigrade. Depending on the power consumption of the heating resistance 38, this process can take e.g. 10-15 minutes.

The chamber pressure is then reduced to a sufficiently low level to start a plasma within the chamber by an RF generator attached to antenna 13 and the chamber 34. Preferable the chamber pressure should be below 500 mT during this plasma pre-conditioning phase 54. The chamber pressure is monitored via a pressure gauge 11. The plasma generated within the chamber generates and homogenously distributes heat within the chamber and further ensures evaporation of any residual water from the medical instruments.

After pre-conditioning liquid hydrogen plasma is injected (70) into a pre-heated vaporizer 32 intermittently in small volumes say in 6-20 pulses with 8-15 sec duration between the pulses in between. The benefits of the pulsed injection is described in the Cummings' U.S. patent. In the vaporizer the sterilant is converted into vapor which is then released to the sterilization chamber.

Following the injection the chamber pressure rises approximately 10-20 Torr pressure to allow diffusion for a period of low pressure diffusion 65. Typically this process lasts about for approximately 4-8 minutes. During this period hydrogen peroxide vapor is expected to diffuse homogenously inside the chamber and into the medical instruments in the $H_2O_2$ permeable pouches. During the $1^{st}$ and $2^{nd}$ diffusion phases 58 and 62 respectively the sterilization chamber 34 temperature and pressure are the critical parameters effecting the sterilization cycle efficacy and controlled by well known means and in a well known process.

Following the low diffusion, conditioned air is introduced into the chamber through a HEPA filter 10 into the chamber via electrically controlled solenoids SL1 (12) and the chamber pressure is raised up to atmospheric pressure 69 which is kept stable for 760 Torr diffusion period 67 for about 2-15 minutes depending on the particular sterilization program selected for a given lumen length and the material of a medical instrument to be sterilized. A short duration may not be sufficient for hydrogen peroxide molecules to penetrate narrow and long lumens despite the increased pressure. The optimum diffusion duration for a given lumen and for a device is established empirically by exhaustive tests carried out by following the half cycle validation guidelines provided by ISO 14937 standards.

This cycle then repeated for further sterilization assurance (see FIG. 3), e.g. vacuuming 60, followed by 2nd injection 72 and 2nd diffusion 62. This phase is followed by evacuation to low vacuum 64 and application of RF energy to generate plasma. The plasma ensures hydrogen peroxide molecules left in the chamber and on the pouches to be decomposed into free radicals and eventually water and oxygen. The free radicals thus generated together with the UV radiated from the plasma further improve the sterilization efficacy.

At the final aeration phase 68 ventilates the chamber and further ensures that the medical equipment to be sterilized is cleaned from any residual excess hydrogen peroxide. During the evacuation any remaining hydrogen peroxide molecules that were not decomposed during the post plasma 64 and left the chamber are trapped within the catalytic converter 44 before extracted by the pump 48 and exhausted via a filter 50.

In the preferred embodiment described above SL1 (12), SL2 (14), SL3 (16) are two way valves used to prevent or admit the flow of liquid, vapor and filtered and dehumidified pure air controlled by dedicated computer, the master controller card 42 which receives input commands via touch sensitive screen graphical user interface 40. These solenoids The solenoid which expose to liquid or vapour sterilant should be made from materials that are chemically resistive to hydrogen peroxide transmission.

Figure 8:
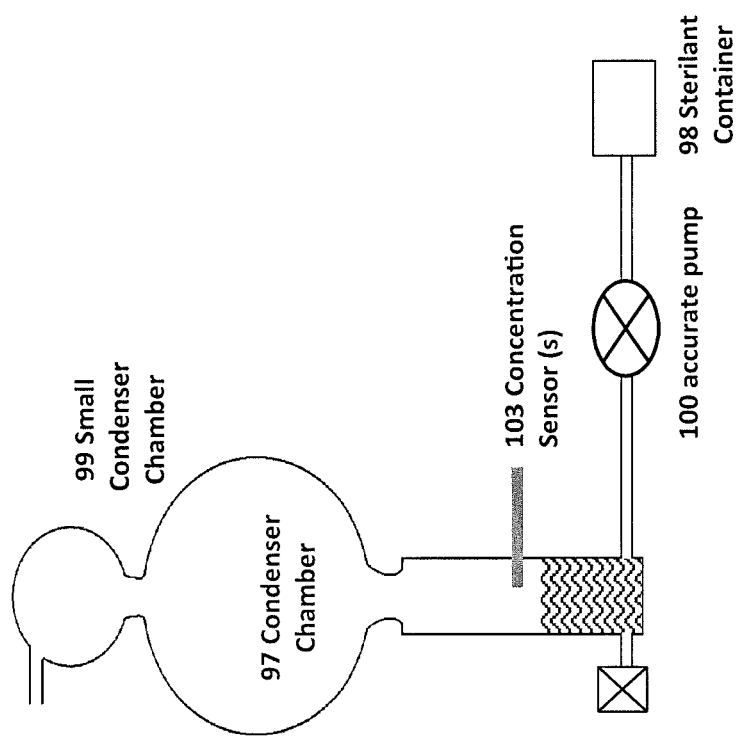
FIG. 8 shows injector-concentrator designed to support multi mode (concentrated and non-concentrated) sterilization program cycles with a accurate sterilant volume delivery pump.

In the plasma sterilizer depicted in FIG. 2, the hydrogen peroxide delivery subsystem 22 delivers a low concentration sterilant liquid from a small container or cartridge to the injector concentrator 20. The concentration of the sterilant within the container or cartridges are kept below 60% due to transport restriction. The delivery process is a well know art and usually involves filling up the injector until a level sensor 28 provides a signal to the master controller 42. It would be possible to fill the injector by transferring the liquid via measured liquid flow via a small pump with associated precision volumetric control unit as depicted in FIG. 8.

In one embodiment the level detection within the injector is performed by placing two stainless steel metal pins opposing to each other with a thickness less than 1 mm to measure resistivity of the medium. If both pins are in hydrogen peroxide liquid then it would present a corresponding circuit a lower resistance.

In one embodiment, if there is an overfill then the solenoid SL2 (73) and solenoid SL3 (75) could be used to make further fine adjustments. For this purpose the SL3 could provides low vacuum suction option as it is connected to the evacuating pump 49 via catalytic converter 44 whereas the SL2 provides atmospheric pressure. By controlling these solenoids in harmony with two way hydrogen peroxide delivery system 89 it is possible to adjust the liquid level via relatively simple and well understood art.

In the disclosed inventions, the concentration of the hydrogen peroxide is a critical parameter. The disclosed injector concentrator (shown separately in FIG. 4A) is used to control this critical parameter. Within this unit the sterilants concentration is increased in a controlled manner up to a pre-determined level say above 80% wt or above 90% weight.

During the concentration process the injector concentrator is kept heated in a standby mode via injector heater 93. Once a fixed amount of sterilant (say 5.2 ml for a sterilizer with a 140 liter sterilization chamber though useable volume may be smaller say 110 Liter due to antenna placed into the chamber for the generation of plasma) has filled into the injector, then the pressure of the concentrator is reduced by intermittently opening and closing SL3 (75). Concurrently the injector heater 93 power is increased to force the liquid sterilant to boil. By controlling the condenser pressure via monitoring the pressure sensor (95) and power input to the heater 93 it is possible to create conditions where major portion of the water within the sterilant is vaporized. During this process the water vapor is then suctioned out via the suction solenoid SL3 (75) intermittently. The condenser is kept at the ambient temperature or kept at a lower temperature (than the injector) with another heater in order to create a temperature gradient encouraging any escaping hydrogen peroxide to condense and return back to the injector while due to low pressure, water continues to remain in vapor phase.

During concentration process the concentration is level is continuously monitored by measuring the electrical resistance of the hydrogen peroxide via sensors placed in the injector.

Figure 5:
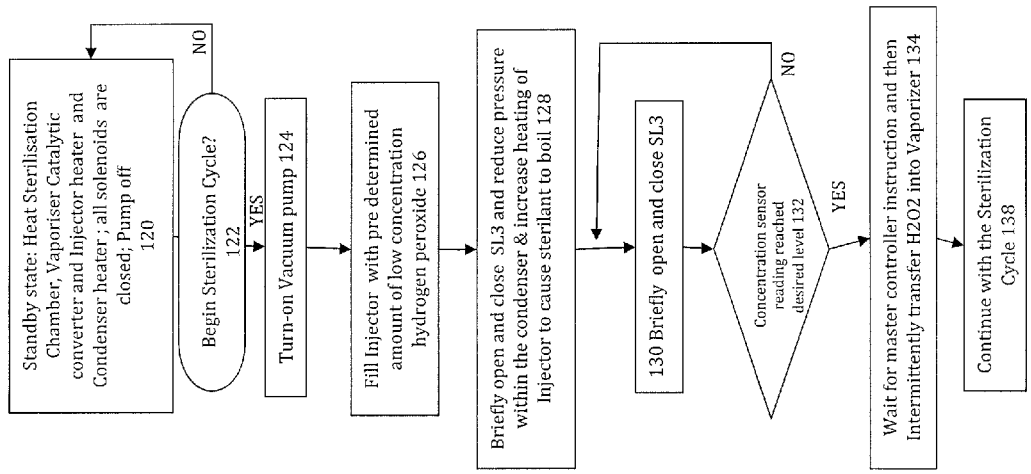
FIG. 5 shows a flow chart of the operation of the injector-concentrator in a preferred embodiment.

FIG. 5 depicts the flow chart of the preferred concentration process.

Typically during the standby state of the sterilizer the sterilization chamber, vaporizer, catalytic converter and Injector concentrator are kept heated at predetermined levels. All solenoids SL1, SL2 and SL3 are s are closed and the pump is turned off.

The sterilization cycle usually starts after the medical instruments are loaded into the sterilization chamber and the door is securely locked via a command on the touch screen attached to the device. Once the "begin sterilization Cycle" command is received 122 the vacuum pump is turned on 124 and subsequently the hydrogen peroxide delivery subsystem delivers pre-determined amount of low concentration hydrogen peroxide liquid into the injector concentrator 126. The amount delivered depends on whether concentrated or non concentrated cycle is selected. The injector heater power is increased from its standby level to a higher operational power and the solenoid SL3 (16) is briefly opened and closed intermittently (said brief period which can be determined empirically) to lower the pressure of the condenser and cause the sterilant to boil 128 FIG. 5. Once the critical low pressure and high temperature is reached the hydrogen peroxide within the injector boils and preferentially water vapor is extracted from the condenser chamber. At this stage it would be beneficial to monitor the condenser pressure via a pressure sensor 15 FIG. 2 to ensure a repeatable process and continue the SL3 process until the pre-determined pressure is reached.

During the concentration the solenoid SL3 (16) is opened and closed intermittently for a brief period to extract vapor wherein said brief period which can be determined empirically. Following this the concentration sensor reading is taken to examine whether the desired concentration level is reached 132. If not reached, then the SL3 operation mention in this paragraph is repeated. When the desired level is reached and then process controller instructs the concentrated sterilant liquid is intermittently transferred into the chamber via vaporizer 32.

The duration of the concentration process can be determined by continuously checking whether the desired concentration level has been reached via well know position sensor means. In this embodiment the level sensors 83 is used for a fixed level concentration. There could be multiple such sensors for different levels of concentration.

In the preferred embodiment the electrical resistance characteristics of the hydrogen peroxide is continuously monitored and upon reaching a desired level say above 80% wt or say above 90% wt via a second level sensor placed at a lower position than the concentration is terminated.

Once the desired concentration level of the sterilant is reached then the liquid sterilant is transferred intermittently into the vaporizer 134 and the diffusion cycle of the sterilization starts 138.

The hydrogen peroxide sterilant is usually available with various amounts of stabilizers (phosphate derivatives etc.) which can vary its electrical resistance characteristics and the rate of its electrical resistance varies with concentration. In the preferred embodiment the electrical characteristics of the particular sterilant used is drawn as a plot against the concentration level. The concentration of the $H_2O_2$ can be measured independently via a densitometer or any other well known means.

In another embodiment the electrical resistance characteristics of the hydrogen peroxide is continuously monitored and upon reaching a desired level around 87-92% wt the concentration is terminated.

In another embodiment the concentration process is terminated when a predetermined volume or weight of sterilant remains in the injector. For this aim the boiling process in the injector can be stopped and the volume of the hydrogen peroxide is measured via electrical level sensors or weight sensors or optically or other well known means. This predetermined volume can be established empirically via repeated experiments involving measuring the density of the remaining liquid sterilant versus the volume and weight (or both) of the remaining sterilant while keeping the concentration process parameters unchanged.

In another embodiment the concentration process is terminated after a fixed duration. This fixed duration can be established empirically by repeated experiments to extract typical durations required to reached desired concentrations.

Figures 4A, 4B:
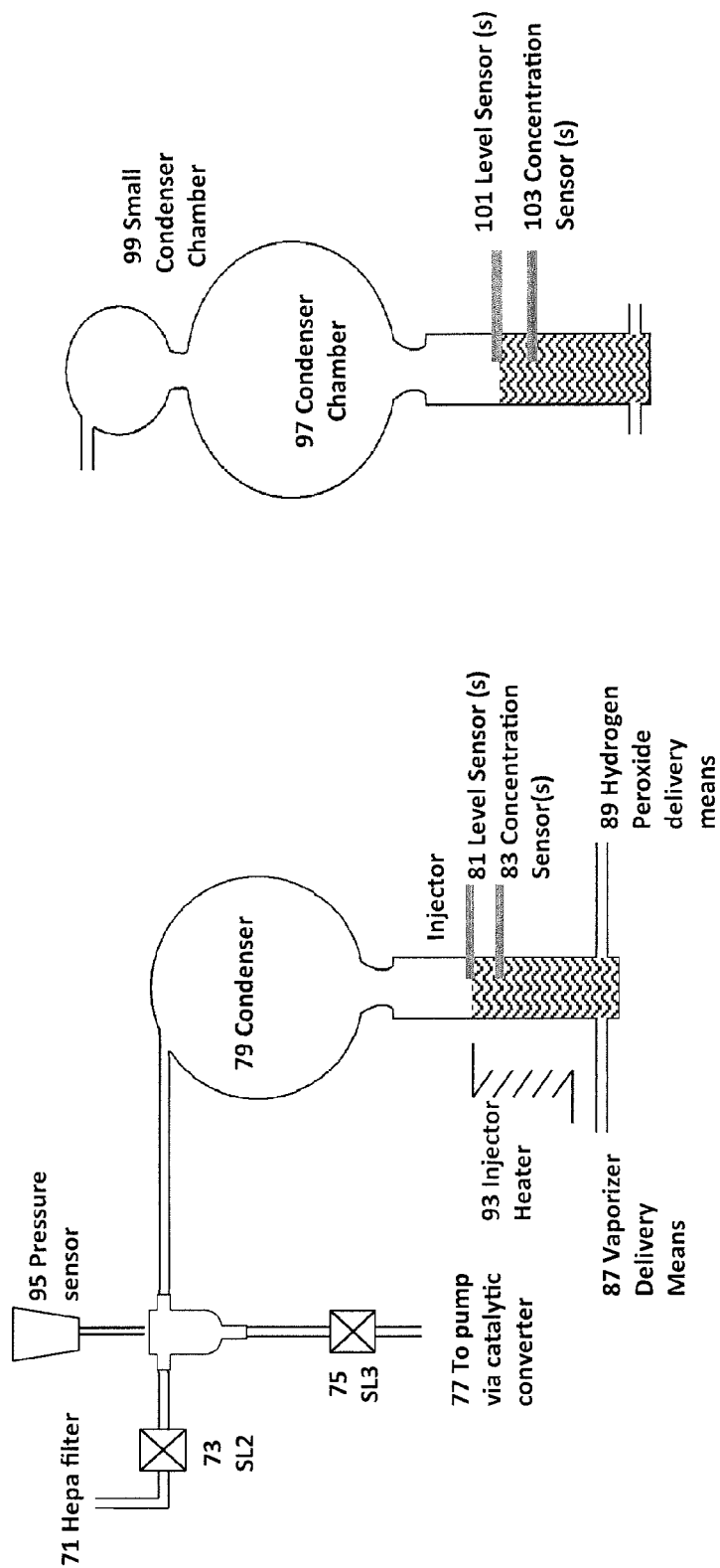
FIG. 4A shows an injector-concentrator embodiment.
FIG. 4B shows an alternative injector-concentrator embodiment.

FIG. 4B shows the schematic of another embodiment of the injector concentrator wherein the main condenser chamber 97 is complemented by a secondary small condenser chamber 99 which may results better condensation efficiency. The liquid concentration is a well known art and the shape and material of the injector concentrator can be designed to further improve the concentration efficiency and hence reduce the duration of the process.

Figure 1:
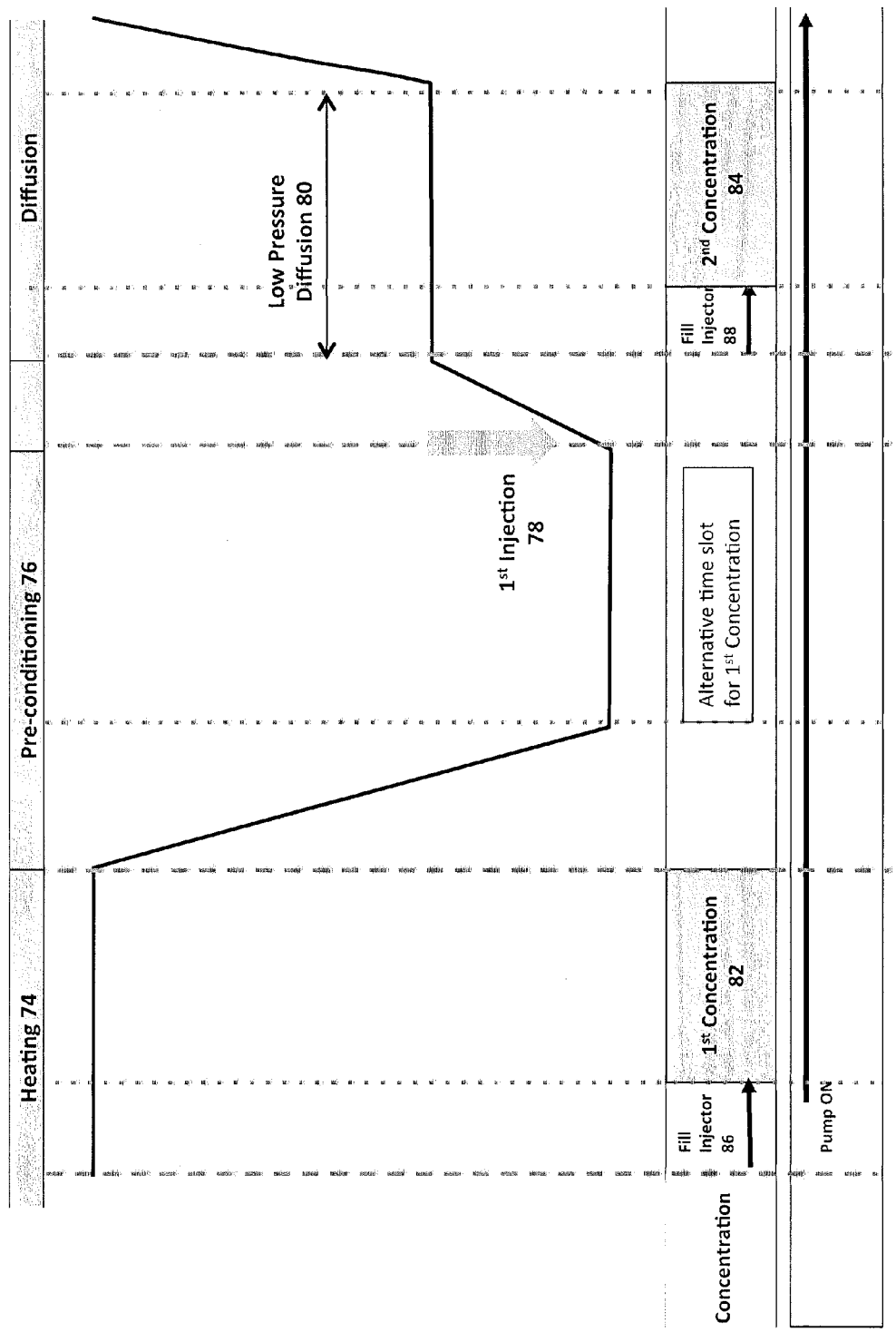
FIG. 1 schematically shows integration of a separate hydrogen peroxide concentration into a typical hydrogen peroxide gas plasma sterilization cycle.
Figure 1A:
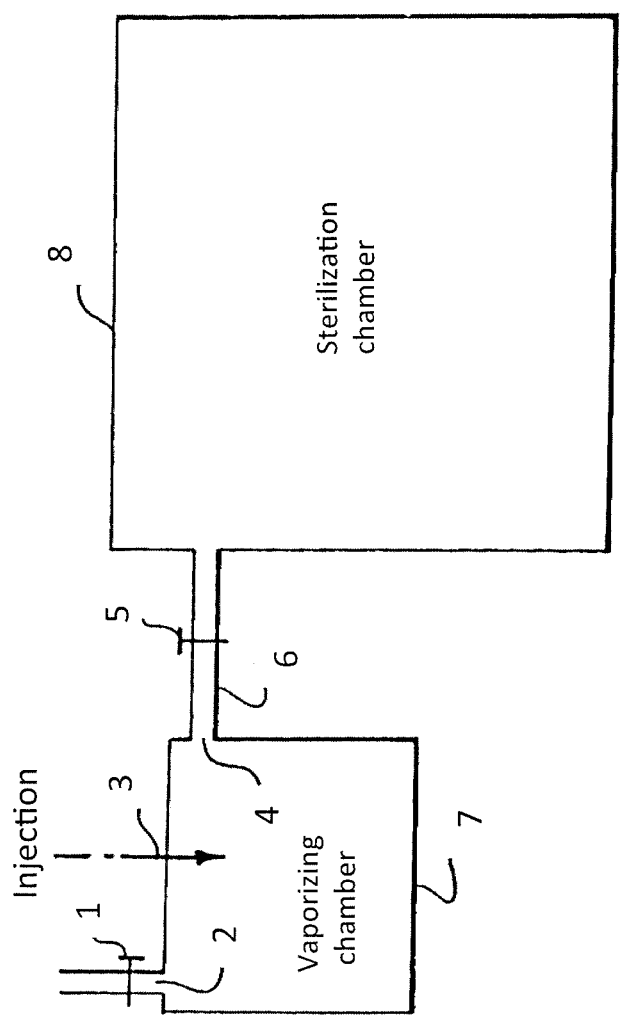
FIG. 1A shows a previously proposed apparatus to concentrating a liquid hydrogen peroxide solution.

As presented earlier in a plasma sterilizer the sterilization cycle is repeated twice for sterilization assurance. In the example of FIG. 1, the concentration process 82 for the first injection 78 is carried out during heating of the sterilization chamber 74. Alternatively the concentration could also be done during the pre-conditioning plasma phase 54 after the gate valve 36 is closed. Duration of the pre-conditioning plasma is about 6-8 minutes and is sufficient for the concentration process which could last 4 to 6 minutes. During heating the temperature of the articles to be sterilized are raised together with the atmospheric temperature within the chamber to 48-55 degree centigrade. During the heating the in order to start the concentration gate valve 36 is closed the pump 48 is turned on 90. Then the injector is filled 86 and the concentration process 82 begins. In the preferred embodiment injector is filled during the heating and the first concentration is performed during the pre-conditioning plasma which requires gate valve to be closed after the initial vacuum. In the preferred embodiment the second concentration for the second cycle is performed during the low pressure low pressure 1st diffusion 80 which typically lasts 8 minutes and provides sufficient time for the concentration process.

In another embodiment it is possible to concentrate the sterilant at double volume which would be sufficient for two injections. In this case the injector concentrator would be designed to hold double amount of sterilant and Vaporizer delivery means 18 only delivers the half of the volume of the concentrated sterilant at each injection.

Figure 6:
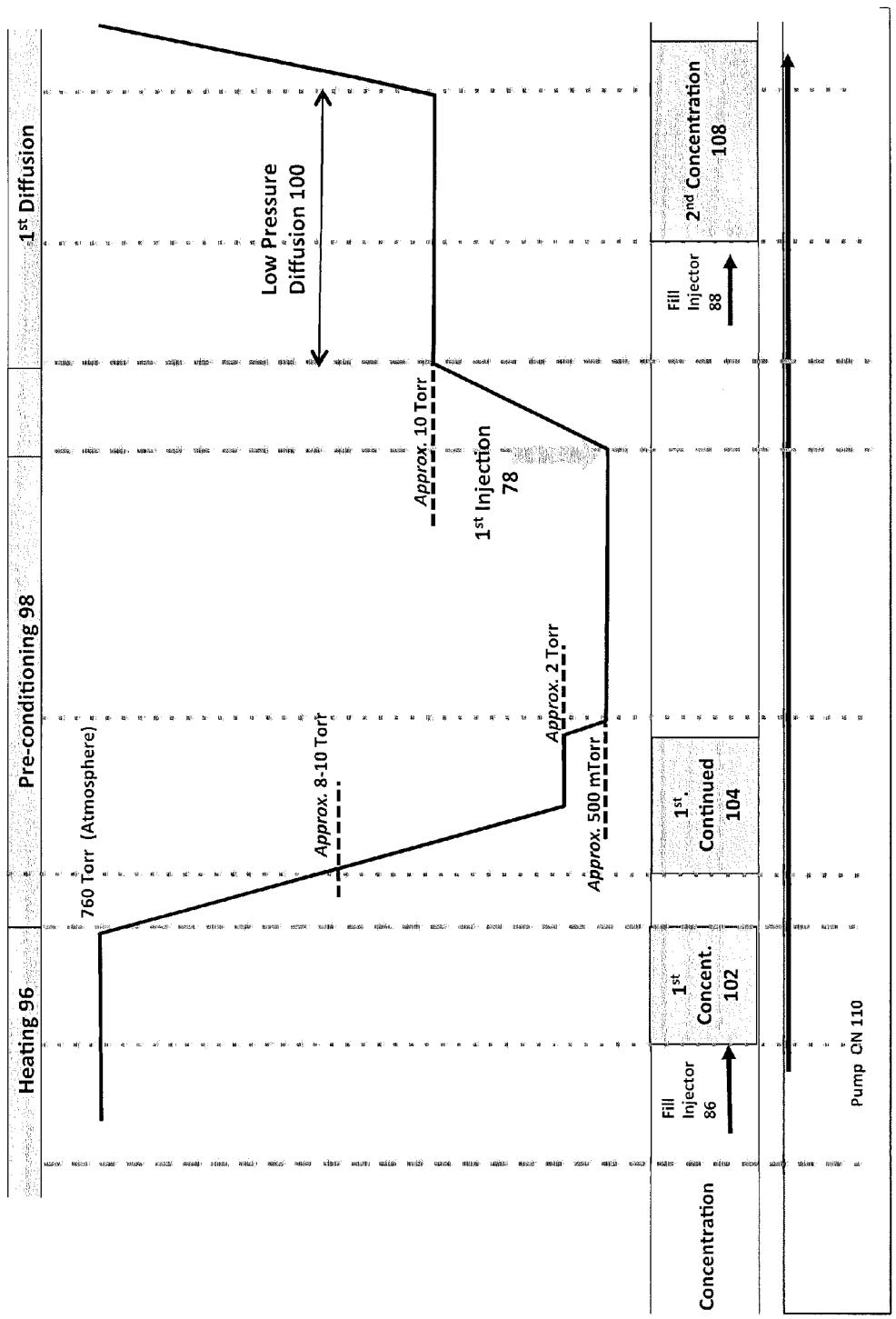
FIG. 6 shows an alternative integration of the hydrogen peroxide concentration into a typical hydrogen peroxide gas plasma sterilization cycle.

FIG. 6 shows an alternative integration of the hydrogen peroxide concentration process into the first sterilization cycle. In this embodiment in order to further reduce the sterilization cycle duration, the concentration process is performed partially during the heating 96 and partially during a portion of the pre-conditioning 98. Because there is only one pump employed which is used for both evacuating the air from the chamber 44 as well as the condenser 24, once the gate valve 36 is opened then the solenoid SL3 becomes ineffective. In this embodiment the concentration process can resume 104 when the chamber pressure drops down to say 8-10 Torr. During the concentration 104 it may not be possible to bring the chamber pressure low enough for the plasma to trigger since the gate vane is open and the water vapor is suctioned from the condenser. However once the concentration is finished the chamber pressure can be brought down to say 500 mT and the plasma starts. A better alternative is to resume the concentration process after closing the gate valve 36 after reaching the vacuum. In preferred embodiment the first concentration is done fully during the pre-conditioning plasma un-interruptedly 54*a* FIG. 3 after closing the gave valve 36 after the vacuum.

Further in the preferred embodiment it is possible to start continue the 2nd concentration 108 even after raising the chamber pressure to the atmospheric level for the high diffusion as depicted in FIG. 6. This scheme offers a solution if the low pressure diffusion duration 107 is too short to accommodate the second concentration 108.

In another embodiment the evacuation of the condenser chamber of the injector concentrator is done by employing a separate pump other than the pump used to evacuate the sterilization chamber. This would allow greater flexibility in deciding the start time of the concentration process. The evacuated vapor does still need through the catalytic converter to trap any hydrogen peroxide which escapes the condenser.

The preferred embodiment has been implemented and tested in Stericool 110S model from GOA Technologies. It has been validated that consistently high concentration level achieved (85-90%) contributed significantly to the sterilization efficacy of the device particularly when used with long lumens. The extent of penetration of hydrogen peroxide into a tube is measured by colorimetrically assaying the amount of hydrogen peroxide deposited on the special purpose hydrogen peroxide chemical indicators placed in standard lumen set.

In order to support sterilization of certain type of medical equipment which may be sensitive to highly concentrator hydrogen peroxide vapor it may be desirable to introduce a special sterilization program for these devices where the concentration level may be set to a lower concentration level say 70% by weight via the means described herein or keep it unchanged. In the disclosed invention the injector concentrator design can be modified to support dual action of concentrated process or non concentrated process or multiple level of concentration on the same device. This means wide range of medical equipment including those sensitive to concentrated hydrogen peroxide vapor can be sterilized within the same equipment by simply adapting an appropriate sterilization program.

Figure 7:
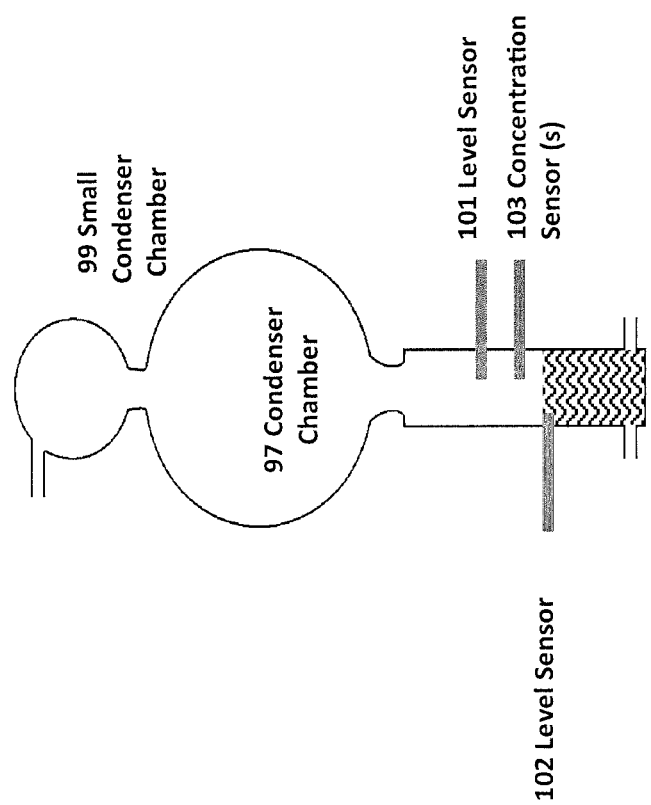
FIG. 7 shows injector-concentrator designed to support multi mode (concentrated and non-concentrated) sterilization program cycles.

When a non-concentrated program is selected the sterilization cycle process will follow the steps described in paragraphs above without a need for the concentration process. For the non-concentrated program the amount of hydrogen peroxide vapor released into the sterilization chamber will be different than the amount released via concentrated program cycle. This requirement can be met by introducing an additional level sensor (102) into the injector design as depicted in FIG. 7 which could be used to limit the sterilant volume allowed into the injector to be at this preset level. In the disclosed embodiment when the non-concentrated program is selected the controlling computer program uses the reading on this secondary level sensor and limits the hydrogen peroxide volume to this level as described in the steps above. The actual amount of hydrogen peroxide used for the non concentrated process would be around 0.015 to 0.04 ml H2O2 per liter of the sterilization chamber volume. Alternatively if a concentrator program is selected than the computer program reads the sensor 101 in FIG. 7.

In another embodiment the concentrated or non-concentrated programs may have different sterilant volume, diffusion time and temperature and chamber pressure. Each of these parameters can be experimentally optimized. Once this optimization is completed than exhaustive tests must be carried out by following the half cycle validation guidelines provided by ISO 14937 standards to validate the each process.

Further in order to assess any damage to the sensitive medical equipment it would be necessary to expose said equipment to repeated sterilization cycles and study the aging under microscope or using other appropriate tools.

In another embodiment the dual purpose injector concentrator is connected to a hydrogen peroxide delivery subsystem which compromise of a accurate liquid volume delivery pump (similar to pharmaceutical volume delivery pumps) connected to the sterilant container as shown in FIG. 8. In this embodiment the concentrated full level sensors 101 (for the concentrated cycle) and 102 (for non concentrated cycles in FIG. 7 are no longer necessary as the admitted H2O2 is already measured accurate volume.

Figure 9:
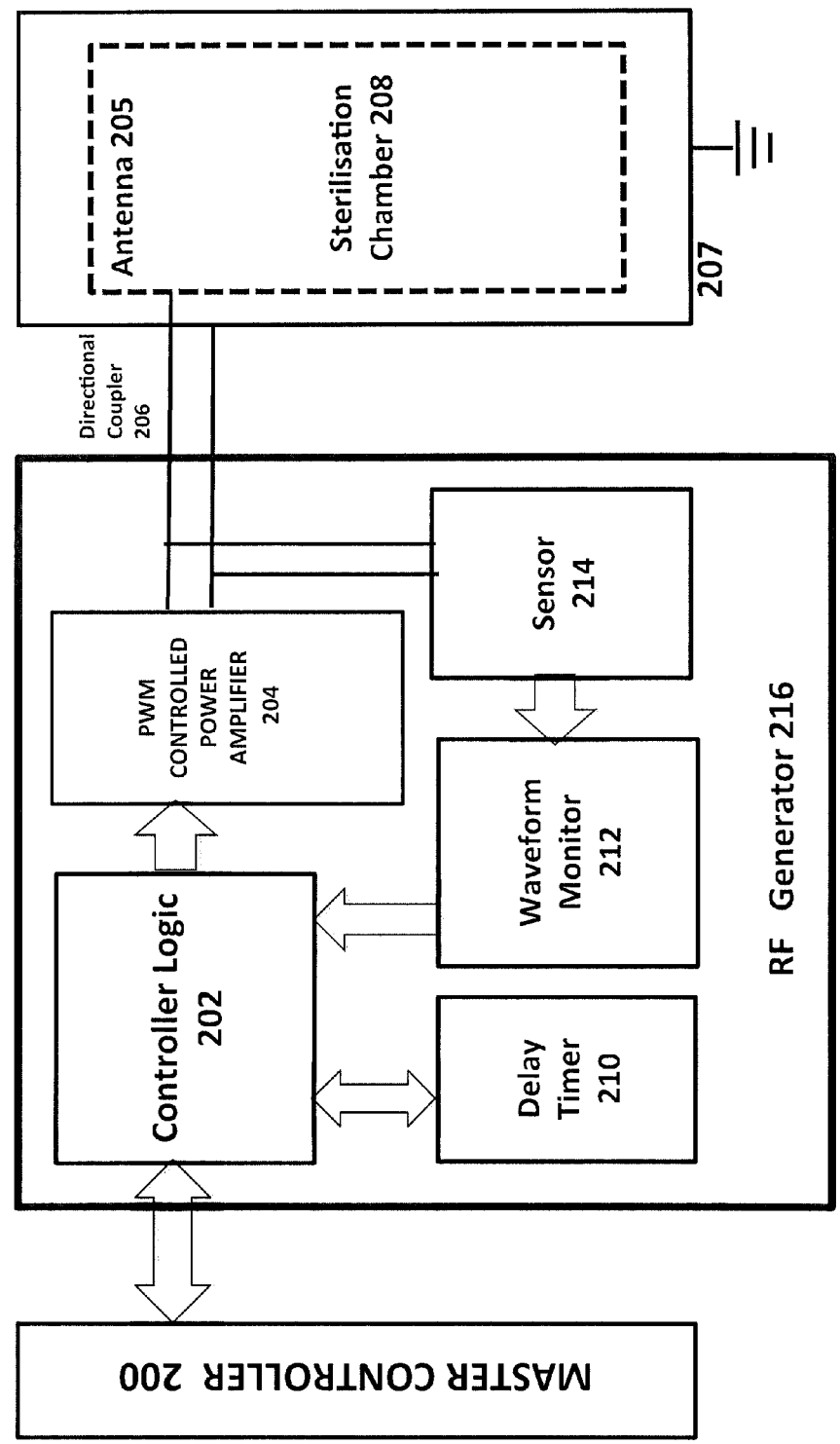
FIG. 9 shows an radio frequency power generator to deliver profiled power between the antenna and the frame of the sterilization chamber to generate a controlled glow discharge within chamber for a controlled duration.

In the described apparatus the glow discharge plasma is generated in a chamber (208 FIG. 9; 34 FIG. 2). The plasma is generated by evacuating the chamber and turning on the power to the electrodes (which are the antenna and the chamber enclosure itself). When used in the present application, the term "plasma" is intended to include any portion of the gas or vapor which contains electrons, ions, free radicals, dissociated and/or excited atoms or molecules produced as a result of the applied electrical field across the antenna 205 FIG. 9 and chamber enclosure 207. The applied field may cover a broad frequency range, however, a radio frequency (say 140 kHz-170 kHz) is commonly used.

The chamber includes radio frequency electrodes in form of an antenna wound around the sides of entire chamber, A radio frequency generator (216, FIG. 9) is coupled to the chamber to deliver the radio frequency power. Further coupling of RF power from the output of the matching network is accomplished by means fine tuning the geometry of antenna. For this aim fix sized holes punched on the antenna and its gap to the chamber enclosure 207 is adjusted. The techniques used in said coupling are well understood by those skilled in the art.

The radio frequency power generator employed in the invention comprised of controller logic 202 (FIG. 9) unit which communicates with the Master Controller 200 and controls the pulse width modulation controlled power amplifier 204.

Pulse width modulation ("PWM") is used to allow the control of the power delivered to the antenna 205. PWM is a modulation technique that conforms the width of the pulse, the pulse duration based on modulator signal information.

The output of the power amplifier is monitored by a sensor unit 214 by capturing its waveform and generating a voltage level. The output of the sensor 214 is fed to the waveform monitor 212 which includes level sensors. The output of the waveform monitor is fed back to the controller logic. The RF generator circuitry also includes a variable delay timer unit 210.

Figure 10:
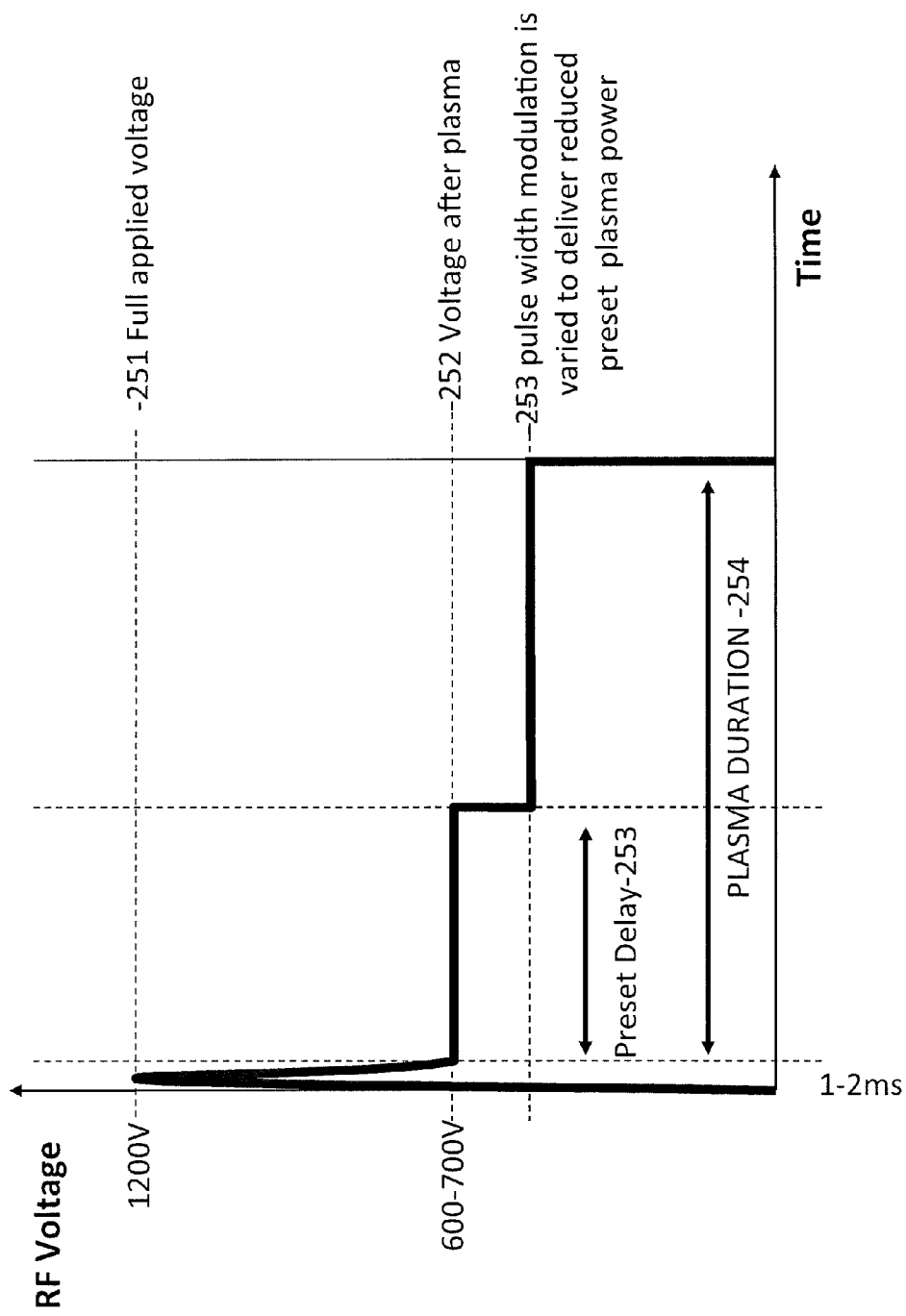
FIG. 10 shows plasma profiling by varying the pulse width modulation output of the RF generator during a plasma phase of a sterilization cycle. When the plasma triggers a new load conditions are presented by the reduction of the applied voltage. By further changing the pulse width modulation of the RF output the power delivered to the antenna is further reduced after a preset delay.

FIG. 10 shows the variation of voltage applied by the RF generator during a plasma phase of a sterilization cycle. The RF voltage drops drastically after the plasma is triggered within the chamber. It is varied by pulse width modulation of the output power of the amplifier 204 after a preset timer delay to optimize its output to the different phases of the sterilization cycle.

Figure 11:
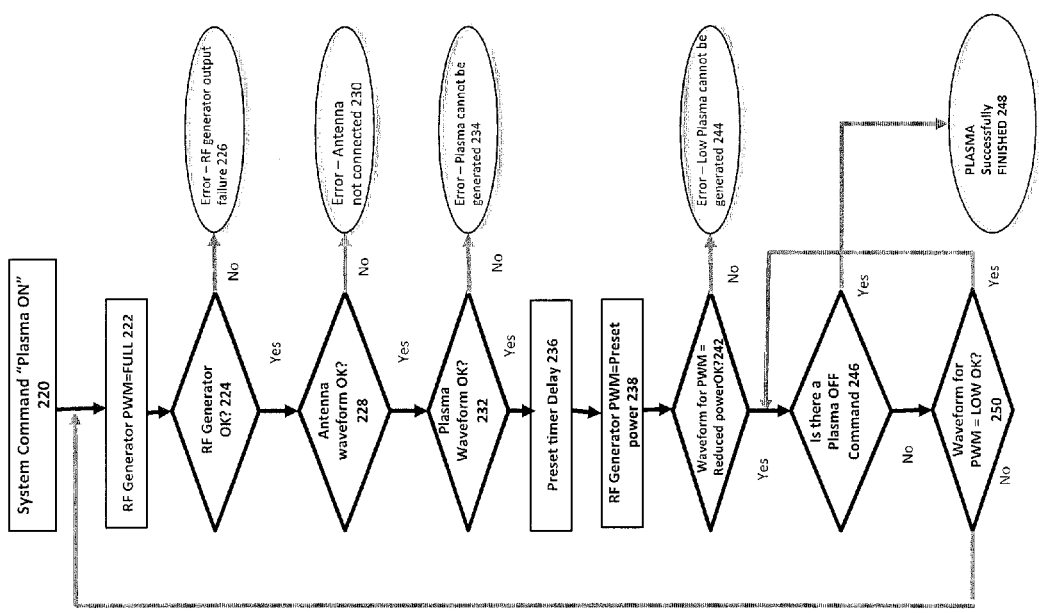
FIG. 11 depicts a plasma profiling process flow chart for plasma power profiling for a given plasma stage by applying different preset delay and preset reduced power for the said stage.
Figure 12:
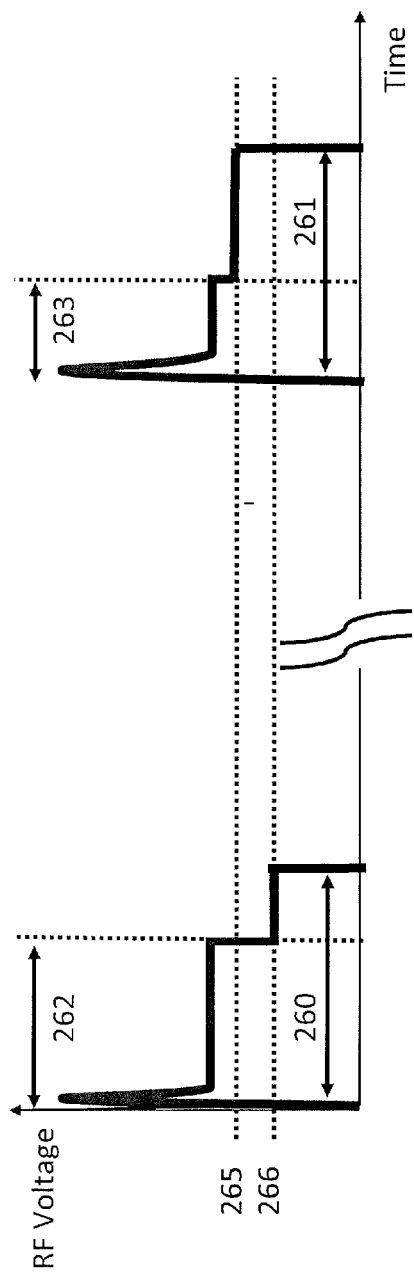
FIG. 12 shows different plasma power profiles for different plasma phases which includes pre-conditioning plasma (pre-plasma) and post-diffusion plasma (post-plasma). Herein different preset delays and different pulse width ratios are applied to minimize etching effects within the chamber for that particular phase.

FIG. 11 depicts a plasma profiling process flow diagram for plasma power profiling for a given plasma stage by applying different preset delay and preset reduced power for the said stage. When plasma is to be generated Master Controller 200 instructs the Controller Logic 202 of the RF generator to initiate the plasma (corresponds to 220 in the process flow chart). The Controller is then sets the output of the pulse width modulated power amplifier to full power. For a 110 Lt sterilizer unit the full power output usually corresponds but not limited to 200 to 400 watts. In one embodiment of the invention when the RF generator delivers full power the initial RF voltage applied to the antenna is raised to 1200 volts 251 as shown in FIG. 10.

As the next step on the flow chart of FIG. 11 RF output of the output amplifier is measured to ensure that the amplifier is functioning correctly 224. If the measurement is not satisfactory an appropriate error message 226 is communicated back to the Master Controller 200.

The waveform monitor 212 unit via a sensor 214 attached to the output of the RF amplifier 204 then checks whether the full power is delivered to the antenna 228 in FIG. 11. If the measurement is not within an expected range than Antenna circuit is faulty and appropriate error 230 is communicated back to the Master Controller.

Once the plasma is ignited the electrical impedance of the plasma circuits changes dramatically forcing the RF voltage down to 600-700 volts within 1-2 milliseconds as shown in FIG. 11.

The waveform monitor which is continuously monitoring the power output waveform via the resonator sensor confirms that the full power is delivered to the antenna 232, if not an appropriate error message 234 is passed to the Master Controller.

Upon delivering the full output power the Controller Logic starts the timer 236 with a preset delay value. The duration of timer delay is set by the Master Controller depending on the phase of the sterilization cycle. After the delay the power output of the RF generator is reduced to a preset level (preset power level 253 in FIG. 10). Said preset power level can be determined experimentally to be the level which cause minimum etching on the medical apparatus and adverse effect on the polymer based medical apparatus yet sufficiently high enough to maintain the plasma glow within the chamber for sterilization (a) to generate sufficient homogenous heat during pre-conditioning and (b) to generate sufficient UV radiations and ionized high energy free-radicals whenever the plasma is on and (c) at the post-diffusion plasma phase to decompose all of the hydrogen peroxide sterilant molecules present in the chamber.

The activation of said preset power output level is further verified by the sensor 214 feeding to the waveform generator 242. An appropriate error message 244 is passed to the Master controller if the result is not satisfactory. The process is continuously monitored 246 so that if the Master Controller instruct to turn the plasma off an appropriate is action taken 248 and the plasma output is cut off. Otherwise the continuity of preset power level of the plasma is monitored 250 and if all parameters within the expected range than the process continues in a loop until the Master Controller instructs otherwise.

In some cases however while setting the preset power level of the RF Generator the glow in the chamber may become extinguished. The waveform generator 250 can easily detect such an undesirable (250 decision NO) event and immediately informs the Controller Logic sets the RF Generator output to sets the full power.

Figure 13:
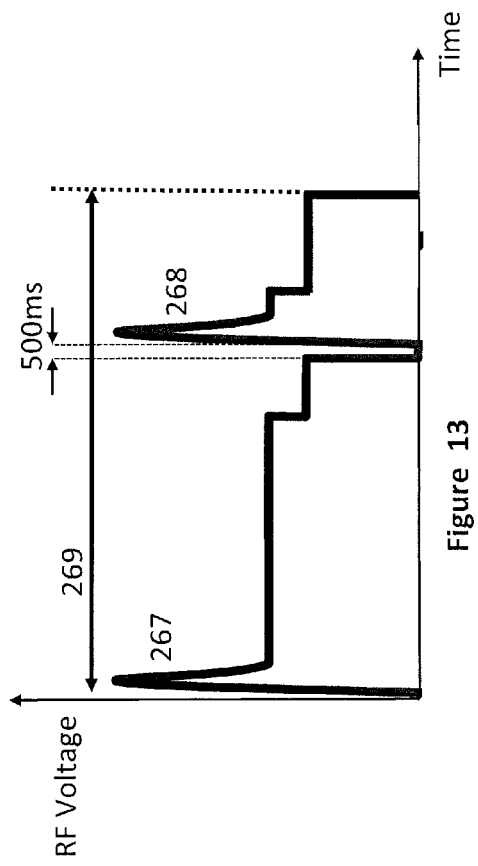
FIG. 13 shows automatic trigger activation in operation if the plasma is extinguished undesirably.

FIG. 13 shows automatic trigger activation in operation if the plasma is extinguished undesirably.

The Controller logic continuously monitors the cycle in every step and the cycle is interrupted whenever the Master Controller instructs to end the plasma process.

The plasma presents different characteristics during the different phases of sterilization program as the gas content of the chamber varies.

Plasma During Pre-Conditioning:

When energy is deposited to air, the air molecules become excited. As air is composed primarily of nitrogen and oxygen excited N2 and O2 molecules are produced. These can react with other molecules, forming mainly ozone and nitrogen oxide. Water vapor when present, may also play a role; its presence is characterized by the hydrogen emission lines. Generally, the radiant species present in atmospheric plasma N2, N2+, O2, NO (in dry air) and OH (in humid air).

The excited nitrogen de-excites primarily by emitting a photon, with emission lines in ultraviolet, visible, and infrared band:

$$N_2' \rightarrow N_2$$

The blue light observed is produced primarily by this process. The spectrum is dominated by lines of single-ionized nitrogen, with presence of neutral nitrogen lines.

The excited state of oxygen is somewhat more stable than nitrogen. While de-excitation can occur by emission of photons, more probable mechanism at atmospheric pressure is a chemical reaction with other oxygen molecules, forming ozone.

$$O_2' + 2O_2 \rightarrow 2O_3 \text{[molar mass 2*48)}$$

Plasma During Post Diffusion:

Literature references indicate that, in a highly simplified form, the reactions in plasma, for which hydrogen peroxide H2O2 serves as a precursor, may be summarized as follows:

$$H_2O_2 \texttt{-----------------} > H_2O_2'$$

$$H_2O_2' \texttt{----------------} > H_2O_2 \text{ Visible and/or UV radiation}$$

$$H_2O_2 \texttt{----------------} > HO' + HO'$$

$$HO' + H_2O_2 \texttt{----} > H_2O + HO_2'$$

HO' refers to the hydroxyl free radical

HO$_2$' refers to the hydroproxyl free radical $H_2O_2{}'$ refers to an electronically excited hydrogen peroxide molecule in which an electron has been elevated to a higher energy level).

As stated above the etching impact of the plasma significantly increase with the molecular mass of the prevailing gas molecules in the chamber. Therefore order to minimizes surface etching it would be highly advantageous to adjust the plasma power profile according to the prevailing molar mass of the gas content during a typical sterilisation cycle.

In one embodiment in during the pre-conditioning phase when there is relatively less presence of heavy ozone (with molar mass of 48) and oxygen molecules ozone and oxygen (32 i.e. two oxygen atoms) in the chamber due to the low pressure higher plasma power is applied for a longer period (i.e. longer preset delay) before reducing the power to heat up the chamber homogenously and to generate more UV and free radicals.

In one embodiment when there are more heavy molecules present within the chamber during after the release of the post-diffusion phase such as (electronically excited hydrogen peroxide molecule with molar mass of 34) it would be more beneficial to reduce the plasma power to a level (i.e. set preset delay shorter say 2 min and preset power lower say ⅓ or ½) which is sufficient to decompose the hydrogen peroxide residual into radicals and generate UV but low enough not to cause any significant surface etching.

The combination of UV light and reactive radicals is complimentary to the hydrogen peroxide vapour for a fast sterilisation processes. The DNA of most of the bacteria can be broken by high energy radiation with wavelengths below 280 nm.

In one embodiment during the pre-conditioning plasma 54 FIG. 3 when there is no hydrogen peroxide is present in the chamber the RF power could kept at high power up to 4-6 minutes and then lowered to a preset power level which is 30 to 50% of the output power and during the post plasma phase 64 of FIG. 3 the output power of the RF amplifier could be reduced to reduced power level which is 30 to 50% after 2-3 minutes.

The disclosed innovations, in various embodiments, provide one or more of at least the following advantages. However, not all of these advantages result from every one of the innovations disclosed, and this list of advantages does not limit the various claimed inventions.

Sterilization of wide range of sensitive medical instruments
Faster throughput;
Better than $10^{-6}$ sterilization;
Shorter cycle time;
Better safety;
Lower cost of consumables;
Better results with articles having long thin lumens;
Faster process with articles having long thin lumens;
Reduced likelihood of handling toxic exhaust and/or byproduct;
Fewer uncontrolled process variables; and/or
Fewer safety concerns.

According to some but not necessarily all embodiments, there is provided: A process for introducing concentrated hydrogen peroxide vapor to interior surfaces of medical instruments with lumens in an evacuated sterilization chamber comprising the steps of: filling an injector concentrator at a predetermined volume of liquid solution of relatively dilute hydrogen peroxide; heating the injector concentrator and evacuating its condenser chamber to preferentially vaporize the water content of the said liquid into a condenser prior to vacuuming said sterilization chamber; intermittently withdrawing a portion of said water vapor from said condenser chamber via vacuum suction to concentrate said hydrogen peroxide remaining in said injector concentrator; terminating said withdrawal of water vapor from said condenser chamber when said remaining hydrogen peroxide is measured to be sufficiently concentrated so as to produce, concentrated hydrogen peroxide greater than about 80% by weight; intermittently transferring the said concentrated hydrogen peroxide liquid in small volumes into a separate pre heated vaporizer connected to the sterilization chamber; and maintaining said hydrogen peroxide vapors in contact with said medical instruments until sterilization is achieved.

According to some but not necessarily all embodiments, there is provided: A sterilization process, comprising the steps, in any order unless specifically stated, of: placing objects to be sterilized into a sterilization chamber; performing a low-pressure evaporation procedure on an initial volume of aqueous hydrogen peroxide which has an initial concentration of less than about 60% wt hydrogen peroxide, to extract water vapor therefrom, without passing the water vapor through the sterilization chamber, until the resulting concentrated hydrogen peroxide is measured to have reached at least a target concentration value; said target concentration value being greater than 80% wt; evacuating said sterilization chamber, and generating a plasma in a space which is continuous with said sterilization chamber for a period; and then vaporizing at least some of the concentrated hydrogen peroxide into said sterilization chamber; holding said sterilization chamber at a pressure of less than 50 Torr for more than 3 minutes, while said concentrated hydrogen peroxide remains present in the vapor phase; and then rapidly increasing the pressure of said sterilization chamber, whereby a net flow of concentrated hydrogen peroxide vapor into the interior of lumens of said objects occurs; wherein said concentrating and vaporizing steps are performed at different locations within a single machine.

According to some but not necessarily all embodiments, there is provided: A sterilization process, comprising the steps, in any order, of: placing objects to be sterilized into a sterilization chamber; performing a low-pressure evaporation procedure on an initial volume of aqueous hydrogen peroxide to extract water vapor therefrom until the resulting concentrated hydrogen peroxide is known to have reached at least a target concentration value; said target concentration value being greater than 80% wt; evacuating said sterilization chamber; transferring at least some of said concentrated hydrogen peroxide into a vaporizer, and vaporizing at least some of the concentrated hydrogen peroxide from said vaporizer into said sterilization chamber; and holding said sterilization chamber at a pressure of less than 50 Torr for more than 3 minutes, while said concentrated hydrogen peroxide remains present in the vapor phase; wherein said concentrating and vaporizing steps are performed within a single machine.

According to some but not necessarily all embodiments, there is provided: A sterilization process, comprising the steps, in any order, of: placing objects to be sterilized into a sterilization chamber; concentrating aqueous hydrogen peroxide until the resulting concentrated hydrogen peroxide is known to have reached at least a target concentration value; said target concentration value being greater than 80% wt; evacuating said sterilization chamber, and vaporizing at least some of the concentrated hydrogen peroxide into said sterilization chamber at less than 50 Torr for a duration and then rapidly increasing the pressure of said sterilization chamber, whereby a net flow of concentrated hydrogen peroxide vapor into the interior of lumens of said objects occurs; wherein said concentrating and vaporizing steps are performed by different parts of a single machine.

According to some but not necessarily all embodiments, there is provided: A sterilization process, comprising the steps, in any order, of: placing objects to be sterilized into a sterilization chamber; concentrating aqueous hydrogen peroxide until the resulting concentrated hydrogen peroxide is known to have reached at least a target concentration value; said target concentration value being greater than 80% wt; evacuating said sterilization chamber, generating a plasma within said chamber for a determined duration, and then vaporizing at least some of the concentrated hydrogen peroxide into said sterilization chamber; and holding a concentrated hydrogen peroxide vapor in said chamber, for long enough to reduce the population bacteria therein by at least a factor of a million; wherein said concentrating and vaporizing steps are performed within a single machine.

According to some but not necessarily all embodiments, there is provided: A sterilization system, comprising, in a single unit: a sterilization chamber; a concentrator which performs a low-pressure evaporation procedure on an initial volume of aqueous hydrogen peroxide, to extract water vapor therefrom until the resulting concentrated hydrogen peroxide is known to have reached at least a target concentration value; said target concentration value being greater than 80% wt; a vaporizer, which vaporizes at least some of the concentrated hydrogen peroxide into said sterilization chamber; and a valve from said chamber to a vacuum manifold, and another valve from said concentrator to said vacuum manifold; wherein said concentrating and vaporizing steps are performed within a single machine.

According to some but not necessarily all embodiments, there is provided: sterilizers, and sterilization methods, which use a novel injector-concentrator arrangement. This arrangement provides accurate control of concentration of the liquid-phase hydrogen peroxide, prior to vaporization of the liquid sterilant into the sterilization chamber. This increases the reliability and efficacy of the sterilization cycle.

According to some but not necessarily all embodiments, there is provided: A process for introducing concentrated hydrogen peroxide vapor to interior surfaces of medical instruments with lumens in an evacuated sterilization chamber comprising the steps of selecting concentrated or non-concentrated sterilization program manually on the user interface screen (40 FIG. 2) appropriate to the medical device that will be sterilized; then if a concentrated program is selected; filling an injector concentrator at a predetermined volume of liquid solution of relatively dilute hydrogen peroxide; heating the injector concentrator and evacuating its condenser chamber to preferentially vaporize the water content of the said liquid into a condenser prior to vacuuming said sterilization chamber; intermittently withdrawing a portion of said water vapor from said condenser chamber via vacuum suction to concentrate said hydrogen peroxide remaining in said injector concentrator; terminating said withdrawal of water vapor from said condenser chamber when said remaining hydrogen peroxide is measured to be sufficiently concentrated so as to produce, concentrated hydrogen peroxide greater than about 80% by weight; alternatively if the non-concentrated program is selected simply filling an injector concentrator at a different predetermined volume of liquid solution of relatively dilute hydrogen peroxide via a help of a secondary level sensor (102 in FIG. 7); then for both concentrated and non-concentrated programs doing the executing the following steps; intermittently transferring the said concentrated hydrogen peroxide liquid in small volumes into a separate pre heated vaporizer connected to the sterilization chamber; and maintaining said hydrogen peroxide vapors in contact with said medical instruments until sterilization is achieved.

The chemical aggressiveness of the hydrogen peroxide may be partially dependent on its injected volume the temperature and the pressure during the diffusion phase. In another embodiment the non-concentrated program may have a higher diffusion pressure and or lower chamber temperature. These parameters can be experimentally optimized to reduce the chemical aggressiveness of the sterilant in its vaporized form on specific sensitive medical equipment and materials. Once such an optimization is completed than exhaustive tests must be carried out by following the half cycle validation guidelines provided by ISO 14937 standards to validate the each process with new parameters.

According to some but not necessarily all embodiments, there is provided: A process for introducing concentrated hydrogen peroxide vapor to interior surfaces of medical instruments with lumens in an evacuated sterilization chamber comprising the steps of selecting concentrated or non-concentrated sterilization program manually on the user interface screen (40 FIG. 2) appropriate to the medical device that will be sterilized; then if a concentrated program is selected not executing the concentration within the unit.

According to some but not necessarily all embodiments, there is provided: A radio frequency power system with a capability of profiling power applied to a plasma in a sterilization system, said sterilization system comprising a chamber, said power system comprising an improved control mechanism wherein the applied power profile is varied by a parameter which is partially in dependence on timing information of plasma power applied during a sterilization cycle that is whether the plasma is applied at the pre-conditioning phase (54 FIG. 3) or at the post plasma (64 FIG. 3) or in some cases during the vacuum phase (60 of FIG. 3).

According to some but not necessarily all embodiments, there is provided: A radio frequency power system with a capability of profiling power applied to a plasma in a sterilization system, said sterilization system comprising a chamber, said power system comprising an improved control mechanism wherein the applied power profile is varied by a parameter which is partially in dependence on constitution of gas within the chamber that is whether the chamber contains more air molecules or water molecules or hydrogen peroxide molecules or any other gas molecules may be introduced into the chamber to improve the sterilization process.

According to some but not necessarily all embodiments, there is provided: A radio frequency power system with a capability of profiling power applied to a plasma in a sterilization system, said sterilization system comprising a chamber, said power system comprising an improved control mechanism wherein the applied power profile is varied by a parameter which is partially in dependence on constitution of gas within the chamber that is whether the chamber contains more air molecules or water molecules or hydrogen peroxide molecules or any other gas molecules may be introduced into the chamber to improve the sterilization process. Said power profile may be varied by a parameter dependent on the initial state of gas content (ratio of the gas molecules) of the chamber prior to application of said plasma power.

According to some but not necessarily all embodiments, there is provided: A radio frequency power system with a capability profiling power applied to a plasma in a sterilization system, said sterilization system comprising a chamber, said power system comprising an improved control mechanism wherein the applied power profile is varied by a parameter in dependence on whether the selected sterilization program is based on concentrated or non-concentrated hydrogen peroxide sterilant.

According to some but not necessarily all embodiments, there is provided: A radio frequency power system with a capability profiling power applied to a plasma in a sterilization system, said sterilization system comprising a chamber, said power system comprising an improved control mechanism wherein the presence of said plasma in the sterilization chamber is repeatedly monitored and reignited if it extinguishes within 0 to 5 minutes of said application of the plasma power.

MODIFICATIONS AND VARIATIONS

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for profiling radio frequency power applied to plasma in a chamber of a sterilizer, said sterilizer comprising a radio frequency power generator configured to apply radio frequency power to said plasma, wherein a radio frequency power profile applied by the radio frequency power generator is varied by a parameter which is at least partially dependent on at least three of the following:
   timing information of sterilization cycle of said sterilizer,
   selection of concentrated or non-concentrated sterilization program,
   constitution of gas within said chamber while the radio frequency power is applied, and
   initial state of gas content of said chamber prior to application of the radio frequency power to said plasma.

2. The method as described in claim 1, wherein the presence of said plasma in the chamber is repeatedly monitored and reignited if it extinguishes within 0 to 5 minutes of application of the radio frequency power.

\* \* \* \* \*